United States Patent [19]

Shoshan

[11] Patent Number: 4,656,130

[45] Date of Patent: Apr. 7, 1987

[54] COLLAGEN COATED CELL GROWTH PLATES

[75] Inventor: Shmuel Shoshan, Jerusalem, Israel

[73] Assignee: Yissum Research Development Company, The Hebrew University of Jerusalem, Israel

[21] Appl. No.: 711,528

[22] Filed: Mar. 14, 1985

[51] Int. Cl.$^4$ .......................... C12Q 1/24; C12M 3/02
[52] U.S. Cl. ...................... 435/30; 435/297; 435/299; 435/311; 435/286
[58] Field of Search ............... 435/297, 298, 299, 300, 435/301, 311, 30, 284, 286; 424/116

[56] References Cited

U.S. PATENT DOCUMENTS

| 2,874,091 | 2/1959 | Fisk | 435/301 |
|---|---|---|---|
| 3,814,670 | 6/1974 | Freake et al. | 435/30 X |
| 3,928,136 | 12/1975 | Launey | 435/299 X |
| 4,090,920 | 5/1978 | Studer, Jr. | 435/300 |
| 4,179,266 | 12/1979 | Lukacsek | 435/299 X |
| 4,250,256 | 2/1981 | Wielinger et al. | 435/300 |
| 4,262,091 | 4/1981 | Cox | 435/299 X |
| 4,352,887 | 10/1952 | Reid et al. | 435/284 X |
| 4,374,121 | 2/1983 | Cioca | 424/116 |
| 4,395,397 | 7/1983 | Shapiro | 435/211 X |

Primary Examiner—Alan Cohan
Assistant Examiner—John A. Rivell
Attorney, Agent, or Firm—Webb, Burden, Robinson & Webb

[57] ABSTRACT

A collagen coated cell growth plate comprises a substrate coated with a storage stable coating of collagen fibrils. The method of preparing the collagen coated cell growth plates comprises dispensing biologically active collagen fibrils suspended in distilled water, onto a tissue culture dish. Thereafter, the dish containing the collagen fibril suspension is placed in a laminar flow hood provided with a sterile air stream and ultraviolet light. The fibrils sediment and adhere to the bottom of the dish, the water evaporates in the sterile air stream and is removed in the laminar flow hood exhaust, and the ultraviolet light ensures that the resulting thin layer of collagen fibrils is sterile and ready for the inoculation of living cells. The method yields a convenient pre-coated cell growth plate which can maintain reasonable shelf life when kept at room temperature without any significant decrease in cell growth support properties.

10 Claims, No Drawings
}

COLLAGEN COATED CELL GROWTH PLATES

BACKGROUND OF THE INVENTION

This invention relates to collagen coated cell growth plates, and particularly to a storage stable, collagenous cell growth coating, deposited on cell growth plates, for culturing cells in vitro.

"Natural insoluble collagen" as used herein means and refers to collagen which cannot be dissolved in an aqueous alkaline or in any inorganic salt solution without chemical modification and includes hides, splits, and other mammalian or reptilian coverings. The primary source of natural insoluble collagen is the corium, which is the intermediate layer of a bovine hide between the grain and the flesh sides.

A process for preparing macromolecular biologically active collagen from natural insoluble collagen is disclosed in U.S. Pat. No. 4,279,812. That patent discloses a process for dissolving and regenerating collagen fiber, which removes substantially all impurities from the collagen source and provides a substantially pure collagen product which is biologically active and substantially non-antigenic.

In general, it has been known for many years that the growth of cells in tissue culture is extensive on collagen gels. Collagenous substrata are effective in promoting cell growth in culture conditions for a variety of cells and cell differentiation. See, *Biochemistry of Collagen*, p. 457, Edited by G. N. Ramachandran and A. H. Reddi, 1976 Plenum Press.

The use of collagen as a cell growth medium has also been disclosed in U.S. Pat. No. 4,352,887 to enable successful culture substrates and culture solutions for in vitro culturing of differentiated cells. As needed, the collagen solutions are disposed in the usual laboratory dishes, such as the Petri dish, and thereafter the cell material is added and permitted to grow. In all instances the collagen is prepared and disposed in the dishes by a separate procedure before use.

A need, therefore, remains for stable, universal, cell growth plates which can be precoated with collagen and which can maintain reasonable shelf life when kept at room temperature without any significant decrease in cell growth support properties.

SUMMARY OF THE INVENTION

A collagen coated cell growth plate comprises a substrate coated with a storage stable coating of collagen fibrils. The method of preparing the collagen coated cell growth plates comprises dispensing biologically active collagen fibrils, suspended in distilled water, onto a tissue culture dish. Thereafter, the dish containing the collagen fibril suspension is placed in a laminar flow hood provided with a sterile air stream and ultraviolet light. The fibrils sediment and adhere to the bottom of the dish, the water evaporates in the sterile air stream and is removed in the laminar flow hood exhaust, and the ultraviolet light ensures that the resulting thin layer of collagen fibrils is sterile and ready for the inoculation of living cells. Prior to dispensing the collagen solution onto the dish, the collagen suspension is prepared by diluting a collagen solution with a weak organic acid to a concentration of about 0.2 percent by weight and then dialyzing the diluted solution against phosphate buffer to an ionic strength of about 0.4 and a pH of 7.2 to 7.7 and preferably to about 7.5. Subsequent dialysis against several changes of cold water yields a delicate suspension of collagen fibrils.

DETAILED DESCRIPTION OF THE INVENTION

The present, most preferred, biologically active collagen for use in coating the cell growth plates is a product sold by the Secol Company of Malvern, Pa. under the trade designation BA-1. BA-1 is derived from natural insoluble collagen as follows.

The natural insoluble collagen is treated with an aqueous solution comprised of an alkali sulfate salt (about 0.5 to 1 molar) and alkali metal hydroxide (about 1.0 to 2.5 molar) for at least forty-eight hours to saponify fats suspended within the natural insoluble collagen. The fat free collagen is then treated with an aqueous solution comprised of a 0.5 to 1.0M alkali metal sulfate for at least four hours to stabilize the interfibrillar bonds between individual polypeptide chains of the collagen. The collagen is then dissolved in an aqueous acid solution.

The alkali sulfates are the alkali metal sulfates, such as sodium sulfate, potassium sulfate, and the alkali earth metal sulfates, such as calcium sulfate, magnesium sulfate and the like. Alkali metal hydroxides useful in the manufacture of BA-1 are sodium and potassium hydroxide. Alkaline earth metal sulfates, such as calcium hydroxide and magnesium hydroxide may be substituted in part for the alkali metal hydroxides, however, sufficient potassium and/or sodium hydroxide must be provided. Alkali metal hydroxide and alkali sulfate should be at an initial pH of about twelve to thirteen.

The other salt constituents may include alkali metal chloride, such as sodium chloride and potassium chloride and alkali earth metal chlorides, such as magnesium chloride, calcium chloride and the like.

In treating the natural insoluble collagen with the aqueous solution of the alkali sulfate salt and the alkali metal hydroxide, the natural insoluble collagen should be cut into pieces which are sufficiently small so that the aqueous solution may penetrate and react therein. The natural collagen pieces should be of ten cubic centimeters or less, and more preferably of five cubic centimeters or less. The treatment should take place at an ambient temperature (i.e., between 15° C. and 30° C.) for at least forty-eight hours in order to completely saponify all of the fat suspended within the natural insoluble collagen and to provide a uniform degree of swelling of the collagen fiber.

After the first treating solution is removed, the collagen is treated with a solution of an alkali metal sulfate or alkali earth metal sulfate or a combination thereof at a substantially neutral pH. The concentration of sulfate should be about 0.5 to 1.0 molar. Thereafter, the collagen is preferably neutralized with an aqueous acid solution having a pH between 3 and 4. The collagen is then washed with cold tap water to remove residual salts. Normally, four such washing cycles are required to remove the residual salts. (The methods set forth hereinabove are known in the art (U.S. Pat. No. 4,374,121) and do not describe elements central to the inventive concept of the present application.)

The collagen is then dissolved in a cold aqueous acid solution; the solution contains about one to five milligrams collagen per milliliter of solution and preferably about two mg./ml. The acids useful in dissolving the collagen fiber are the weak organic acids, such as acetic, citric, lactic, ascorbic and tartaric acids. Preferably the pH is adjusted to below four in order to obtain good solubility and the final pH of the aqueous solution should be about three to four.

The collagen solution is then dialyzed, using a suitable dialysis membrane, against a cold phosphate buffer such as potassium phosphate, the ionic strength of which is about 0.3–0.5 and preferably 0.4 and the pH of which is 7.2 to 7.7 and preferably 7.5. The collagen solution is then dialyzed against several changes of cold distilled water until a delicate suspension of native collagen fibrils is formed. The suspension forms after approximately 18–24 hours. The suspension is then dispensed onto a plastic Petri dish, or other suitable culture dish or support structure. The dish is then placed in a laminar flow hood which is equipped to generate a form of sterilizing radiation such as ultraviolet radiation. The laminar flow hood is also equipped to direct a sterile air stream therethrough and exhaust the stream therefrom. The dish and cell growth medium is, accordingly, sterilized in the hood by the sterilizing radiation before, during or after the sedimentation of the collagen fibrils and the evaporation of the aqueous phase of the suspension into the air stream. After the evaporation of most or all of the water and completion of the irradiation sterilization, a thin layer of collagen fibrils adheres firmly to the substrate, and the cell growth medium comprised of the biologically active sterile precipitated collagen and the laboratory dish substrate can then be prepackaged and maintained at room temperature for extended periods of time with no significant decrease in cell growth support properties.

The invention will be more fully described with reference to the specific examples herein set forth.

EXAMPLE I

Secol BA-1 collagen solution was diluted with cold 0.4M. acetic acid to a concentration of two mg./ml. (0.2 percent by weight) and was dialyzed against a 0.16M. cold potassium phosphate buffer to an ionic strength of 0.4 and a pH of 7.6. The solution was then dialyzed against four changes of cold distilled water, over a period of 22 hours, until a delicate suspension of native collagen fibrils was formed. The suspension was then dispensed into Petri dishes, 35 mm. and 60 mm., into which 0.8 ml. and 1.5 ml. of the collagen suspension were added, respectively. The open dishes were put in a laminar flow hood and were flushed with a stream of sterile air for one hour. As the water evaporated, a very thin layer of collagen fibrils sedimented and adhered tightly to the plastic. The dishes were then irradiated with ultraviolet light for three hours. The dishes were hermetically sealed and stored for eight months.

Epidermal cells were obtained from the skin of guinea pig ears and from the gingiva of dogs and the cells were inoculated onto separate dishes of the cell culture medium. One ml. of DMEM [Dubecco's Minimal Essential Medium], supplemented with 10% FCS (fetal calf serum), was added to the dish. Cell attachment, growth and spreading were measured and examined microscopically. Twenty percent of the total cells inoculated attached themselves to the precoated dishes and continued to grow and spread, reaching almost complete confluency after ten days.

EXAMPLE II

A delicate suspension of collagen fibrils was prepared as set forth in Example I, the collagen being that of guinea pig skin, extracted with 0.5M. acetic acid at 0°–4° C. Plates containing 96 wells were prepared as set forth in Example I, each well receiving 0.5 ml. of the collagen suspension. Ten hybridomas were inoculated onto each of the 96 wells (each well having 0.5 ml. DMEM supplemented with 10% FCS added just before inoculation) and satisfactory cloning occurred in twelve days despite the absence of any additional media (such as macrophage conditioned media).

Although the invention has been described with reference to specific materials and specific times and temperatures, the invention is to be limited only insofar as is set forth in the accompanying claims.

I claim:

1. A collagen coated cell growth plate for in vitro culturing of cells comprising a coating consisting essentially of a storage-stable biologically active collagen, with said coating being supported on a substrate.

2. A collagen coated cell growth plate of claim 1, wherein said storage-stable biologically active collagen coating comprises a thin layer of dried collagen fibrils firmly attached to said substrate.

3. The collagen coated cell growth plate of claim 2, said substrate being a plastic tissue culture dish.

4. A method of preparing a storage stable, collagen coated cell growth plate comprising:
   A. forming a suspension which consists essentially of collagen fibrils;
   B. dispensing the resultant biologically active collagen suspension onto a plate; and
   C. evaporating the aqueous phase of said suspension to form the cell growth medium.

5. The method of claim 4, said suspension of collagen fibrils including about 0.05 to 0.5 percent by weight solids of collagen.

6. The method of claim 5, wherein said suspension of collagen fibrils is formed by dialyzing a biologically active collagen solution against several changes of cold water.

7. The method of claim 6, including sterilizing said collagen fibrils and said plate with sterilizing radiation.

8. The method of claim 7, including sterilizing said collagen fibrils and said plate with ultraviolet radiation.

9. The method of claim 8, said collagen solution being prepared by diluting aqueous collagen with a weak acid and dialyzing the diluted aqueous collagen against a phosphate buffer to a pH between 7 and 8.

10. The method of claim 9, said weak acid being organic and selected from the group consisting of acetic, citric, lactic, ascorbic, and tartaric acid.

* * * * *